US010640598B2

(12) United States Patent
Anderson

(10) Patent No.: US 10,640,598 B2
(45) Date of Patent: *May 5, 2020

(54) RESIN BLENDS OF RESORCINOL DIPHTHALONITRILE ETHER WITH BISPHENOL M DIPHTHALONITRILE ETHER AND/OR BISPHENOL T DIPHTHALONITRILE ETHER

(71) Applicant: 3M INNOVATIVE PROPERTIES COMPANY, St. Paul, MN (US)

(72) Inventor: Benjamin J. Anderson, Eden Prairie, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/078,104

(22) PCT Filed: Mar. 30, 2017

(86) PCT No.: PCT/US2017/024947
§ 371 (c)(1),
(2) Date: Aug. 21, 2018

(87) PCT Pub. No.: WO2017/173040
PCT Pub. Date: Oct. 5, 2017

(65) Prior Publication Data
US 2019/0055338 A1  Feb. 21, 2019

Related U.S. Application Data

(60) Provisional application No. 62/475,396, filed on Mar. 23, 2017, provisional application No. 62/348,477, (Continued)

(51) Int. Cl.
C08G 16/02 (2006.01)
C08G 73/00 (2006.01)
(Continued)

(52) U.S. Cl.
CPC ........ C08G 16/0231 (2013.01); C07C 255/54 (2013.01); C07C 323/32 (2013.01); C08G 73/00 (2013.01); C08L 61/00 (2013.01)

(58) Field of Classification Search
CPC ............................ C07C 323/32; C07C 255/54
See application file for complete search history.

(56) References Cited

U.S. PATENT DOCUMENTS 3,429,722 A  2/1969  Economy
3,496,250 A  2/1970  Czerwinski
(Continued)

FOREIGN PATENT DOCUMENTS

CN  105348734  2/2016
JP  62-149723  7/1987
(Continued)

OTHER PUBLICATIONS

Takekoshi, et al., "Polymer Syntheses via Aromatic Nitro Displacement Reaction," Journal of Polymer Science: Polymer Chemistry Edition, vol. 18, No. 10, 1980, pp. 3069-3080.
(Continued)

Primary Examiner — Michael M Dollinger
(74) Attorney, Agent, or Firm — Adrian L. Pishko

(57) ABSTRACT

A resin blend is provided including a blend of resorcinol diphthalonitrile ether resin and a bisphenol M diphthalonitrile ether resin. Another resin blend is provided including a blend of resorcinol diphthalonitrile ether resin and a bisphenol T diphthalonitrile ether resin. The resin blends prior to cure have more favorable processing and curing properties compared to the resorcinol diphthalonitrile resin alone, enabling greater ease in manufacturing.

14 Claims, 1 Drawing Sheet

Related U.S. Application Data filed on Jun. 10, 2016, provisional application No. 62/316,248, filed on Mar. 31, 2016.

(51) Int. Cl.
*C07C 255/54* (2006.01)
*C07C 323/32* (2006.01)
*C08L 61/00* (2006.01)

(56) References Cited

U.S. PATENT DOCUMENTS

| | | | | |
|---|---|---|---|---|
| 3,956,320 | A | * | 5/1976 | Heath ............ C07C 65/24 |
| | | | | 549/241 |
| 4,223,123 | A | | 9/1980 | Keller |
| 4,304,896 | A | | 12/1981 | Keller |
| 4,408,035 | A | | 10/1983 | Keller |
| 4,587,325 | A | | 5/1986 | Keller |
| 4,764,578 | A | | 8/1988 | Malinge |
| 5,003,039 | A | | 3/1991 | Keller |
| 5,312,887 | A | * | 5/1994 | Papathomas ..... C08G 73/0655 |
| | | | | 252/182.21 |
| 5,780,154 | A | | 7/1998 | Okano |
| 6,297,298 | B1 | | 10/2001 | Keller |
| 8,921,510 | B1 | * | 12/2014 | Keller ............. C08G 73/024 |
| | | | | 528/210 |
| 9,221,970 | B2 | | 12/2015 | Schultz |
| 2012/0245253 | A1 | | 9/2012 | Schultz |
| 2014/0275472 | A1 | | 9/2014 | Keller |
| 2015/0267022 | A1 | * | 9/2015 | Hu .................. C08J 9/14 |
| | | | | 442/1 |

FOREIGN PATENT DOCUMENTS

| | | |
|---|---|---|
| JP | 2008-530309 | 8/2008 |
| WO | WO 2006/086758 | 8/2006 |
| WO | WO 2011-050121 | 4/2011 |
| WO | WO 2014-051523 | 4/2014 |
| WO | WO 2017-172515 | 10/2017 |
| WO | WO 2017-173195 | 10/2017 |

OTHER PUBLICATIONS

Canlica, "Synthesis, characterization and electrochemical, and electrical measurements of novel 4,4'-1isopropylidendioxydiphenyl bridged bis and cofacial bis-metallophthalocyanines (Zn.Co)," Polyhedron, 2008, vol. 27, No. 7, pp. 1883-1890, XP022627496.

Derradji, "Effect of silane surface modified titania nanoparticles on the thermal, mechanical, and corrosion protective properties of a bisphenol-A based phthalonitrile resin," Progress in Organic Coatings, 2016, vol. 90, pp. 34-43.

Derradji, "High performance ceramic-based phthalonitrile micro and nanocomposites," Materials Letters, 2016, vol. 182, pp. 380-385.

Derradji, "New oligomeric containing aliphatic moiety phthalonitrile resins: their mechanical and thermal properties in presence of silane surface-modified zirconia nanoparticles," Iranian Polymer Journal, 2016, vol. 25, No. 6, pp. 503-514.

Derradji, "Thermal and Mechanical Properties Enhancements Obtained by Reinforcing a Bisphenol-A Based Phthalonitrile Resin With Silane Surface-Modified Alumina Nanoparticles," Polymer Composites, 2017, pp. 1549-1558.

Dominguez, "Low-melting Phthalonitrile Oligomers: Preparation, Polymerization and Polymer Properties," High Performance Polymers, 2006, vol. 18, No. 3, pp. 283-304.

Dominguez, "Properties of phthalonitrile monomer blends and thermosetting phthalonitrile copolymers," Polymer, 2007, vol. 48, No. 1, pp. 91-97.

Hamciuc, "Poly(1,3,4-oxadiazole-ether-imide)s and their polydimethylsiloxane-containing copolymers," European Polymer Journal, 2007, vol. 43, No. 11, pp. 4739-4749, XP022318829.

Hamciuc, "Poly(ether-imide) and poly (ether-imide)-polydimethylsiloxane containing isopropylidene groups," Polymer Bulletin, 2008, vol. 59, pp. 825-832. XP019561586.

Hsiao, "Synthesis and Characterization of Polyimides Based on Isopropylidene-containing Bis(ether anhydride)s," Journal of Polymer Research, 1997, vol. 4, No. 3, pp. 183-190, XP019221958.

Keller, "High temperature resorcinol-based phthalonitrile polymer," Polymer, 2005, vol. 46, pp. 4614-4618.

Laskoski, "Improved Synthesis of Oligomeric Phthalonitriles and Studies Designed for Low Temperature Cure," Polymer Chemistry, 2014, vol. 52, pp. 1662-1668. XP055380215.

Laskoski, "Synthesis and Properties of a Bisphenol A Based Phthalonitrile Resin," Journal of Polymer Science, Part A: Polymer Chemistry, 2005, vol. 43, No. 18, pp. 4136-4143.

McKeown, "The Synthesis of Symmetrical Phthalocyanines," The Porphyrin Handbook, Phthalocyanines: Synthesis, 2003, vol. 15, pp. 61-124.

Sharman, "Synthesis of Phthalocyanine Precursors," The Porphyrin Handbook, Phthalocyanines: Synthesis, 2003, vol. 15, p. 1-60.

Takekoshi, "Synthesis of High Performance Aromatic Polymers via Nucleophilic Nitro Displacement Reaction," Polymer Journal, 1987, vol. 19, No. 1, pp. 191-202.

Zhou, "Study on One Phthalonitrile Resin System Suitable for RTM Process," ECCM15—15th European Conference on Composite Materials, Venice, Italy, Jun. 24-28, 2012, pp. 1-8.

International Search report for PCT International application No. PCT/US2017/24947 dated Jun. 21, 2017, 3 Pages.

International Search report for PCT International application No. PCT/US2017/024006 dated Jun. 6, 2017, 5 Pages.

International Search report for PCT International application No. PCT/US2017/025233, dated Jun. 19, 2017, 5 Pages.

* cited by examiner

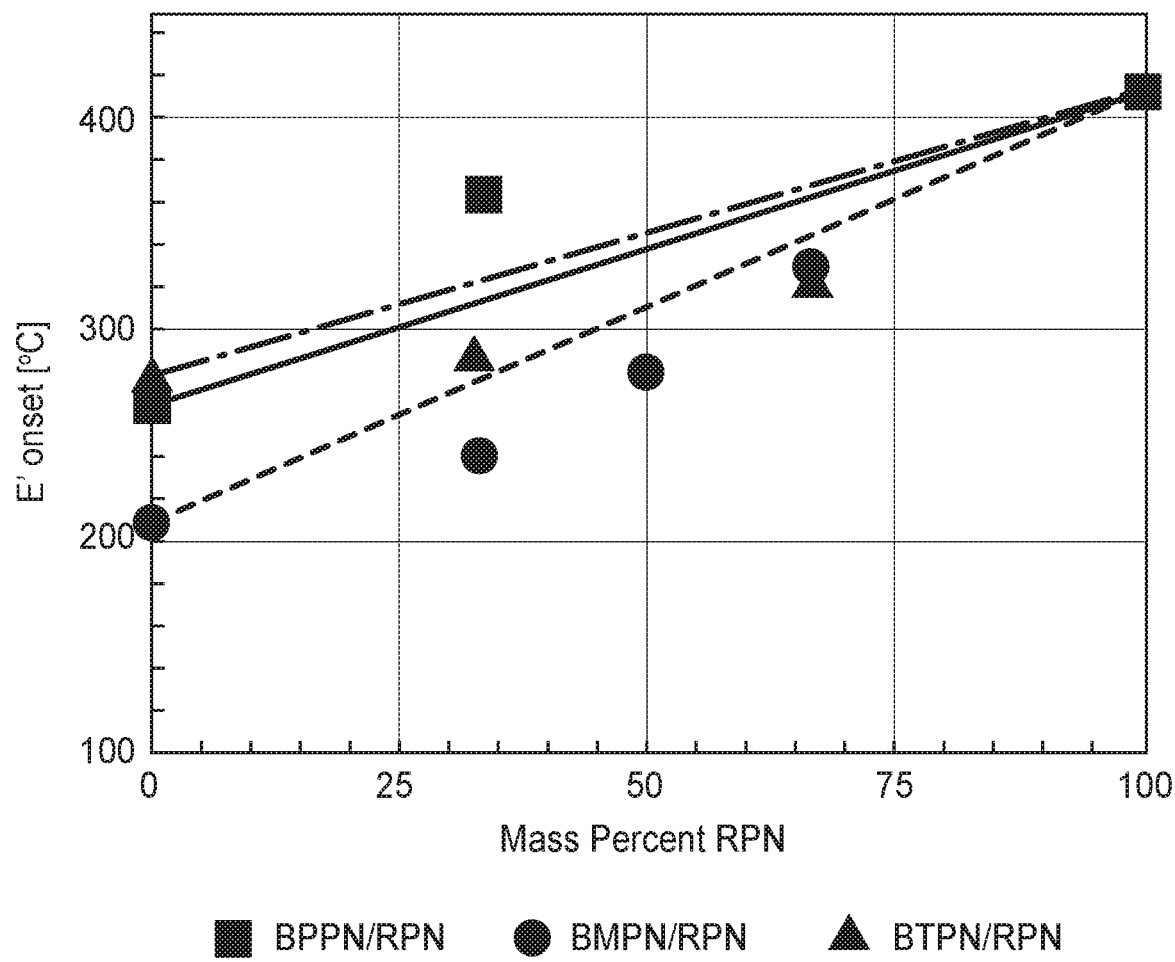

RESIN BLENDS OF RESORCINOL DIPHTHALONITRILE ETHER WITH BISPHENOL M DIPHTHALONITRILE ETHER AND/OR BISPHENOL T DIPHTHALONITRILE ETHER

CROSS REFERENCE TO RELATED APPLICATIONS

This application is a national stage filing under 35 U.S.C. 371 of PCT/US2017/024947, filed Mar. 30, 2017, which claims the benefit of U.S. Application No. 62/316,248, filed Mar. 31, 2016, U.S. Application No. 62/348,477, filed Jun. 10, 2016, and U.S. Application No. 62/475,396, filed Mar. 23, 2017, the disclosures of which are incorporated by reference in their entirety herein.

FIELD

The present disclosure relates to resin blends, including resin blends that improve the processing of resorcinol diphthalonitrile ether resins.

BACKGROUND

Temperature resistant polymer networks are critical for an increasing number of industrial market applications. Applications are diverse from building and construction, electronics packaging, energy and power generation, and transportation. As the environmental temperature of an application increases, the number of available materials able to meet requirements shrinks rapidly.

Phthalonitrile (PN) resins are a class of network forming resins that when polymerized supply excellent thermal stability and degradation resistance, yet commercialization of phthalonitrile resin technology and use is hindered by poor processing properties, high cost, and high temperature autoclave cures. Phthalonitrile resins have high melt temperatures due to the rigid structure of many phthalonitrile molecules which incorporate a large percentage of aromatic structures to maintain the thermal performance of the phthalonitrile polymerized network. The phthalonitrile moiety is also rigid and planar and has a tendency to crystallize. These molecular structure attributes contribute to the high melt temperature of multifunctional PN resins. The high cost of the resin is driven by resin synthesis which utilizes higher cost starting materials (similar to anhydride and imide resins) and multistep synthesis routes. A high glass transition temperature of the polymerized resin imparts excellent thermal stability at high service temperatures, but also contributes to the need for high temperature multistep autoclave cures under inert atmosphere to achieve near full conversion.

SUMMARY

Resin blends are described that provide improved processing of resorcinol diphthalonitrile ether resins. The present disclosure is directed to a resin blend comprising a blend of resorcinol diphthalonitrile ether with bisphenol M diphthalonitrile ether and/or bisphenol T diphthalonitrile ether. In certain embodiments, the resin blend can further include a catalyst, a curative, a toughener (e.g., toughening agent), a filler, additional phthalonitrile, or combinations thereof.

In a first aspect, a resin blend is provided comprising a blend of resorcinol diphthalonitrile ether resin and a bisphenol M diphthalonitrile ether resin. The bisphenol M diphthalonitrile ether resin is of Formula I:

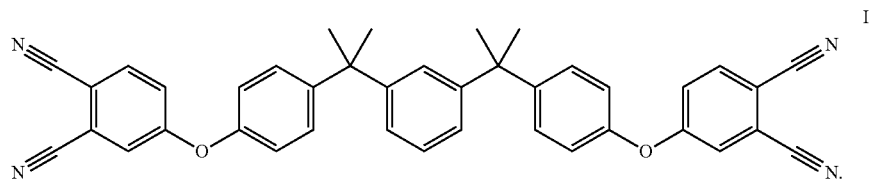 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

In a second aspect, a resin blend is provided comprising a blend of resorcinol diphthalonitrile ether resin and a bisphenol T diphthalonitrile ether resin. The bisphenol T diphthalonitrile ether resin is of Formula II:

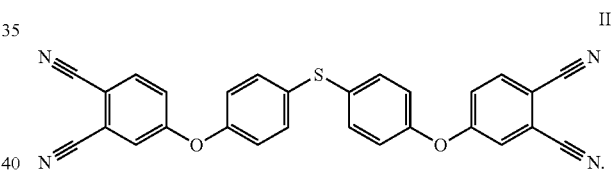

Temperature resistant polymer networks are critical for an increasing number of market applications. As the environmental temperature of an application increases, the number of available materials able to meet requirements shrinks rapidly. The present blends are useful for applications in which a temperature resistant polymer is beneficial.

It was discovered that there remains a need for improving processing of phthalonitrile resins. The present disclosure overcomes difficulties noted for processing phthalonitrile resins, such as high melt temperatures. The use of higher molecular weight phthalonitrile (PN) reactive monomer resins as single component resins and as a component of PN resin blends provides for improved processing, polymerization and end use properties of PN cured polymer networks.

BRIEF DESCRIPTION OF THE DRAWINGS

FIG. 1 is a graph of E' onset temperature of resorcinol diphthalonitrile ether, bisphenol M diphthalonitrile ether, bisphenol T diphthalonitrile ether, and bisphenol P diphthalonitrile ether, as well as blends of resorcinol diphthalonitrile ether with each of bisphenol M diphthalonitrile ether bisphenol T diphthalonitrile ether, and bisphenol P diphthalonitrile ether.

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example "A and/or B" means only A, only B, or both A and B.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

As used herein, the term "phthalonitrile" is inclusive of compounds and polymers having the characteristic benzene derivative having two adjacent nitrile groups. In the illustrated phthalonitrile group, R is for instance and without limitation, ether, thioether, aryl, alkyl, halogen, amine, ester, or amide, heteroalkyl, (hetero)hydrocarbyl.

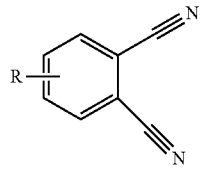

As used herein, "bisphenol M diphthalonitrile ether" refers to bis(3,4-dicyanophenyl) ether of bisphenol M.

As used herein, "bisphenol T diphthalonitrile ether" refers to bis(3,4-dicyanophenyl) ether of bisphenol T.

As used herein, "bisphenol P diphthalonitrile ether" refers to bis(3,4-dicyanophenyl) ether of bisphenol P.

As used herein, "resorcinol diphthalonitrile ether" refers to bis(3,4-dicyanophenyl) ether of resorcinol.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, Si, P, and N, and both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of (hetero)hydrocarbyl alkyl and aryl groups, and hetero(hetero)hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero)hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

As used herein, the term "residue" is used to define the (hetero)hydrocarbyl portion of a group remaining after removal (or reaction) of the attached functional groups, or the attached groups in a depicted formula. For example, the "residue" of butyraldehyde, $C_4H_9$—CHO is the monovalent alkyl $C_4H_9$—. The residue of phenylene diamine $H_2N$—$C_6H_4$—$NH_2$, is the divalent aryl —$C_6H_4$—.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

The present disclosure is directed to resin blends comprising a blend of a resorcinol diphthalonitrile ether resin with bisphenol M diphthalonitrile ether resin, bisphenol T diphthalonitrile either resin, or a combination thereof.

Phthalonitriles are an ideal precursor resin for bulk polymerization reactions due to the addition nature of the phthalonitrile polymerization, advantageous for avoiding unbound reaction byproducts that can weaken the network, leach out of the network, and volatilize at high temperatures. Phthalonitriles undergo an addition cure reaction when promoted by a catalyst or curative. Known catalyst systems for phthalonitrile polymerization promote the tetracyclization of four phthalonitrile moieties into a phthalocyanine ring (McKeown, N. B., *The Synthesis of Symmetrical Phthalocyanines*, in *The Porphyrin Handbook*, K. M. Kadish, K. M. Smith, and R. Guilard, Editors. 2003, Academic Press: Amsterdam. p. 61-124). The phthalocyanines can exist in one of two forms: the metal free (PcH2) or the metal containing (PcM) phthalocyanine. PcH2 may be formed from the addition of base, an alcohol, and heat, or the addition of a suitable reducing agent and heat. These conditions may be satisfied through the addition of an amine base with a primary alcohol (e.g. C1-C5 alcohols). The base catalyzes the formation of a PcH2 and the oxidation of an alcohol to an aldehyde. A suitable reducing agent (e.g., hydroquinone or 1,2,3,6-tetrahydropyridine) able to supply the two electrons and two protons formally needed for PcH2 formation will also lead to cyclotetramerization. PcM may be formed by the addition of metal, organometals or metal salts and heat. The metals coordinate with the central four nitrogens of the phthalocyanine ring. Depending on the coordination state, a metal may interact with more than one phthalocyanine ring giving rinse to stacked phthalocyanine structures. Many metals have been shown to result in cyclotetramerization (ibid.). The downside of these catalyst systems for bulk polymerization reactions is often the evolution of volatiles.

In the absence of a primary alcohol able to undergo oxidation to an aldehyde, primary amines act as phthalonitrile curatives and give rise to an N-substituted-poly(3-iminoisoindolenine) linked polymer network when a multifunctional phthalonitrile resin is employed (U.S. Pat. No. 4,408,035 (Keller) and U.S. Pat. No. 4,223,123 (Keller et al.)). The lack of an alcohol hinders the formation of PcH2 phthalocyanine ring. Primary amines that have shown good reactivity with phthalonitriles are based on aniline. Higher molecular weight and lower volatility aniline functional curatives are typically desired to avoid loss of the curative during polymerization. Dianiline based curatives can be of value due to a higher aniline functionality per weight of the curative. The primary amine promoted phthalonitrile cure reaction proceeds at an appreciable rate between temperatures of 200° C. to 250° C. Amine cured phthalonitrile polymerized networks have demonstrated excellent thermal stability imparted by a high glass transition temperature, good thermal and thermoxidative degradation resistance, plus are inherently non-flammable, and have low moisture uptake. However, current resin technology is limited by long high temperature multistep autoclave cure schedules due to a high glass transition temperature of over 400° C. (U.S. Pat. No. 4,223,123 (Keller et al.)).

Resorcinol diphthalonitrile ether (RPN) has achieved commercial significance and offers a melt temperature of 185° C. and a low melt viscosity, compared to other higher molecular weight phthalonitrile resins. An RPN cured network exhibits a high glass transition temperature of over 400° C. (Keller, T. M. and D. D. Dominguez, *High temperature resorcinol-based phthalonitrile polymer*. Polymer, 2005. 46(13): p. 4614-4618). Bisphenol A diphthalonitrile ether (BAPN) is another well-known resin with a melt temperature of 195° C. A BAPN cured network also exhibits a high glass transition temperature of over 400° C. (Laskoski, M., D. D. Dominguez, and T. M. Keller, *Synthesis and properties of a bisphenol A based phthalonitrile resin*. Journal of Polymer Science Part A: Polymer Chemistry, 2005. 43(18): p. 4136-4143). The high glass transition temperature ($T_g$) of each of the RPN and BAPN cured networks necessitates a multistep cure procedure up to 425° C. under inert autoclave conditions to overcome vitrification hindering polymer network formation and to minimize network degradation at cure temperatures above 300° C. It has been found that phthalonitrile resin technology that combines liquid PN resins at temperatures below 200° C. with PN cured polymer networks with glass transition temperatures of less than 300° C. would be useful; for instance, PN resins that can be processed as liquids below the cure reaction temperature window of 200° C. to 250° C. and form polymer networks with lower glass transition temperatures that avoid vitrification and enable out-of-autoclave cure at lower temperatures without the need of an inert atmosphere.

Traditional approaches employed in attempts to tune the $T_g$ of polymer networks have not shown the ability to successfully tune the $T_g$ of amine cured phthalonitrile networks. One such approach employs resin blends of more molecularly rigid resins (e.g., biphenyl PN) with resins that are more molecularly flexible (e.g., oligomeric RPN(n=4)). The blending of two or more resins has been discovered to be a useful technique for the frustration of resin crystallization of high temperature melting resins. The high melt temperatures of phthalonitrile resins creates a small processing window between the resin melt and cure exotherm, however. Lower molecular weight phthalonitrile resins with low melt temperatures relative to other phthalonitrile resins are preferred in phthalonitrile blends due to their lower melt viscosities and the ability to blend resins at lower temperatures. A second approach employs a reduction in the cross-link density through the incorporation of higher molecular weight reactive monomers (e.g., RPN based and BAPN based oligomers). RPN and BAPN oligomers have much lower softening temperatures, (40° C. and 75° C., respectively), compared to RPN and BAPN, which offers a greater resin processing window below network polymerization temperatures.

Studies of these two approaches with PN resins have not demonstrated an ability to moderate the $T_g$ of PN polymerized networks. When applying the first approach, PN blends of biphenyl PN with RPN(n=4) oligomers did not exhibit a reduction in $T_g$ of the blend network (Dominguez, D. D. and T. M. Keller, *Low-melting Phthalonitrile Oligomers: Preparation, Polymerization and Polymer Properties*. High Performance Polymers, 2006. 18(3): p. 283-304; and Dominguez, D. D. and T. M. Keller, *Properties of phthalonitrile monomer blends and thermosetting phthalonitrile copolymers*. Polymer, 2007. 48(1): p. 91-97). When applying the second approach, higher molecular weight RPN and BAPN based oligomers did not produce a reduction in the glass transition temperature of the polymerized resin, and still required high temperature post cures under inert autoclave conditions (Laskoski, M., D. D. Dominguez, and T. M. Keller, *Synthesis and properties of a bisphenol A based phthalonitrile resin*. Journal of Polymer Science Part A: Polymer Chemistry, 2005. 43(18): p. 4136-4143; and Dominguez, D. D. and T. M. Keller, *Properties of phthalonitrile monomer blends and thermosetting phthalonitrile copolymers*. Polymer, 2007. 48(1): p. 91-97).

The present disclosure demonstrates in at least certain embodiments the ability to tune the glass transition temperature of high $T_g$ amine cured phthalonitrile networks (e.g., RPN) through the incorporation of other phthalonitrile resins that are found to exhibit lower glass transition temperatures for their respective homopolymer networks. This is illustrated, for example, by resin blends of RPN with higher molecular weight phthalonitrile resins: bisphenol P diphthalonitrile ether (BPPN), bisphenol T diphthalonitrile ether (BTPN) and bisphenol M diphthalonitrile ether (BMPN). BMPN and BTPN resins have been found to be surprisingly more effective in moderating the glass transition temperature in a blend network than BPPN, when blended with RPN as an exemplary high $T_g$ network forming resin. The characteristic glass transition temperatures of BPPN, BTPN and BMPN homopolymer networks have been found to be significantly lower than other previously known phthalonitrile cured networks that do not exhibit a softening temperature (Keller, T. M. and D. D. Dominguez, *High temperature resorcinol-based phthalonitrile polymer*. Polymer, 2005. 46(13): p. 4614-4618; and Dominguez, D. D. and T. M. Keller, *Properties of phthalonitrile monomer blends and thermosetting phthalonitrile copolymers*. Polymer, 2007. 48(1): p. 91-97). In addition, the ability to utilize these resins in blends to tune the $T_g$ of blend networks to achieve lower $T_g$ out-of-autoclave processed networks is shown in the Examples below.

In certain embodiments, resin blends of RPN, BPPN, BTPN and BMPN are cured in an air convection oven up to 300° C. and post cured in an inert atmosphere tube furnace up to 350° C., 375° C. and 400° C. as required to complete the cure of the resin. The high network rigidity of PN cured networks necessitates cure temperatures to exceed the tan δ peak temperature of the network to achieve near full polymerization in a reasonable amount of time. Complete cure of the resin is qualified by successive dynamic mechanical heating ramps of cured networks. Long time post cures are usually avoided due to evidence of non-negligible weight loss experienced by the PN cured networks based on isothermal gravimetric analysis measurements under nitrogen leading to networks that have undergone network degradation. Weight loss occurs even at temperatures as low at 350° C. when post cured for an extended period of time (i.e., several hours) under an inert nitrogen atmosphere. Weight loss of the network is accompanied by an increase in stiffness, implying that network degradation is contributing to the increase in stiffness during elevated temperature post cures in addition to further phthalonitrile reaction. The complete cure of RPN and resin blends that contained high fractions of RPN is often difficult to achieve due to the low molecular weight of the resin, which quickly creates vitrification issues during cure and requires higher temperatures for phthalonitrile reactive ends to achieve enough mobility to continue polymerization.

When BPPN was polymerized with a dianiline curative [e.g. 4,4'-(1,3-phenylenedioxy)dianiline, bis[4-(4-aminophenoxy)phenyl]sulfone, 2,2-bis[4-(4-aminophenoxy)phenyl]propane] it was found to produce a network polymer with an E' onset of 264° C. and tan δ peak of 287° C. The lower $T_g$ of the BPPN cured network enables the cure of BPPN to be completed out-of-autoclave in an air convection oven at temperatures up to 300° C. Higher temperature post cures at 350° C. and 375° C. were not found to result in a shift in tan δ. A high melt temperature of 213° C. inhibits liquid processing of BPPN at temperatures below 200° C. away from the resin cure exotherm (i.e., between 200° C. and 250° C.), making BPPN of less use as a single component curable resin unless a less active curative or catalyst is employed. The blending of BPPN as a resin system component to produce lower $T_g$ PN cured networks with RPN as a representative high $T_g$ network producing resin produced a small reduction in $T_g$. As shown in FIG. 1, the $T_g$ of the BPPN/RPN (2:1 blend by mass) was higher than an ideal $T_g$ based on the linear mass combination of the resins (see, e.g., the square located above the solid ideal line). The BPPN resin proved to be less effective than ideal in moderating the $T_g$ of a high $T_g$ PN resin. The result appears to be in agreement with the result of Laskoski et al., who show that bisphenol A based oligomers, sharing a similar chemical backbone structure to BPPN, did not demonstrate a moderation of $T_g$ with an increase in resin molecular weight (Laskoski, M., D. D. Dominguez, and T. M. Keller, *Synthesis and properties of a bisphenol A based phthalonitrile resin*. Journal of Polymer Science Part A: Polymer Chemistry, 2005. 43(18): p. 4136-4143).

Bisphenol T diphthalonitrile ether (BTPN) resin is of Formula II:

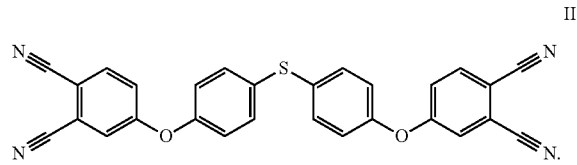 [SMILES: N#Cc1ccc(Oc2ccc(Sc3ccc(Oc4ccc(C#N)c(C#N)c4)cc3)cc2)cc1C#N]

BTPN is another PN resin that has a low resin melt temperature of 178° C. When polymerized with a dianiline curative [e.g. 4,4'-(1,3-phenylenedioxy)dianiline, bis[4-(4-aminophenoxy)phenyl]sulfone, 2,2-bis[4-(4-aminophenoxy)phenyl]propane], BTPN was found to produce a network polymer with an E' onset of 279° C. and tan δ peak of 312° C. The higher $T_g$ of the BTPN homopolymer network required a higher temperature post cure up to 350° C. for one hour under an inert atmosphere to complete the network polymerization. RPN and RPN/BTPN blends were cured in an air convection oven up to 300° C. and post cured in an inert atmosphere tube furnace at 350° C., 375° C. and 400° C. as required to complete the cure of the resin. Resin blends of BTPN and RPN produced lower melting resin blends due to frustration of resin crystallization in the blend, which improves the processability of the blends compared to the individual resins. The glass transition temperatures of the blend networks were between the homopolymer network glass transition temperatures, yet surprisingly fell below an ideal linear combination of the resin blend composition, as shown in FIG. 1 (see, e.g., the triangles located below the dash-dot ideal line). BTPN can thus be effective in moderating the $T_g$ of high $T_g$ producing PN resins. In any embodiment, a weight ratio of the resorcinol diphthalonitrile ether (RPN) resin to the bisphenol T diphthalonitrile ether (BTPN) resin ranges from 10:90 to 90:10, inclusive; or from 15:85 to 85:15, inclusive; or from 25:75 to 75:25, inclusive; or from 30:70 to 70:30, inclusive.

The high $T_g$ of the BTPN network makes this resin less ideal for the development of lower $T_g$, out-of-autoclave polymer network blends, however. A higher temperature post cure above 300° C. was needed to complete the cure of the BTPN homopolymer network in a reasonable period of time.

Bisphenol M diphthalonitrile ether (BMPN) resin is of Formula I:

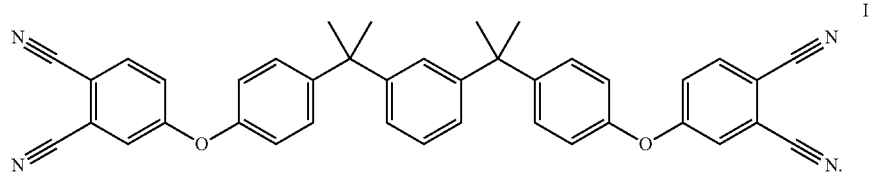 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

BMPN has a melt temperature of 160° C. and was found to have a chemical structure that hinders crystallization, enabling a supercooled liquid state at temperatures lower than the melt temperature. These properties demonstrate the value of BMPN in terms of resin processing as a single component resin and as a resin blend component. When blended with other PN resins, BMPN was discovered to effectively frustrate the crystallization of other higher melting PN resins and resist self-crystallization even at high amounts of BMPN in a PN resin blend (i.e., demonstrated by differential calorimetry measurement of resin blend melt transitions). When polymerized with a dianiline curative [e.g., 4,4'-(1,3-phenylenedioxy)dianiline, bis[4-(4-aminophenoxy)phenyl]sulfone, or 2,2-bis[4-(4-aminophenoxy)phenyl]propane], the BMPN polymerized network was found to have an E' onset of 209° C. and a tan δ peak of 229° C. The glass transition temperature of the BMPN homopolymer network is thus substantially lower than other PN resins.

As a $T_g$ modifying resin, BMPN proved to be the most useful when compared to BPPN and BTPN in the formulation of phthalonitrile resin blends with a higher $T_g$ network forming resin for achieving glass transition temperatures below 300° C. that are out-of-autoclave curable. BMPN/RPN blend glass transition temperatures were also found to surprisingly fall below a linear combination of the resin blend composition, showing BMPN to be an effective resin for moderating the $T_g$ of high $T_g$ producing PN resins as shown (see, e.g., the circles located below the dashed ideal line in FIG. 1). In any embodiment, a weight ratio of the resorcinol diphthalonitrile ether (RPN) resin to the bisphenol M diphthalonitrile ether (BMPN) resin ranges from 10:90 to 90:10, inclusive; or from 15:85 to 85:15, inclusive; or from 25:75 to 75:25, inclusive; or from 30:70 to 70:30, inclusive. BMPN blends with tan δ peaks of less than 300° C. were able to be cured under out-of-autoclave conditions in an air convection oven. Higher cure temperatures over 300° C. up to 350° C. may also be achievable out-of-autoclave for short dwell times. If greater thermal stability is needed where an autoclave cure is required, resin blends with lower amounts of BMPN may produce networks with glass transition temperatures over 350° C. that take advantage of the low melt temperature and slow crystallization time of BMPN for improved processing of PN resin blends (e.g., two component and multicomponent blends) while still achieving a high glass transition temperature. Thus, according to at least some embodiments of the present disclosure, the $T_g$ of a PN polymerized network with varying amount of BMPN can be effectively tuned to temperatures of less than 300° C. for out-of-autoclave cure conditions and to temperatures of greater than 300° C. for extreme thermal stability where an autoclave cure is of value.

The low $T_g$ of the BMPN polymerized network also enables BMPN to modify the $T_g$ of other PN resins as a function of composition (e.g., BPPN and BTPN). The ability of BMPN to effectively moderate the $T_g$ of higher $T_g$ network forming resins is surprising when compared to BPPN, which shares the same molecular formula but is connected in a meta configuration on the central phenyl ring, as compared to a para configuration in BPPN. It has been discovered that the meta connectivity of the BMPN has a profound impact on the segment mobility in BMPN cured networks, indicative of the significantly lower $T_g$ compared to other PN cured networks and the strong ability to moderate the $T_g$ of PN blend networks.

The results described herein for network blends that incorporate BTPN and BMPN demonstrate the ability of these two resins in resin blends, unlike BPPN and other previously studied PN resins, to enable and further the usability of phthalonitrile resins and their polymerized networks. BTPN and BMPN have been found to efficiently moderate the glass transition temperature of at least certain high $T_g$ forming PN resins. BMPN is better suited as a resin blend component for producing out-of-autoclave blended networks due to the low $T_g$ of the BMPN cured homopolymer network. BMPN is an effective resin for producing phthalonitrile resin blends that hinder crystallization more so than other low melting PN resins, thus enabling liquid resins at temperatures below the melt temperatures of the component resins, yet also shows an ability to controllably adjust the glass transition temperature of blend networks as a function of resin blend composition. BMPN is therefore the preferred resin over BTPN for moderating the glass transition temperature of PN cured polymer networks, for some applications.

In certain embodiments, the resin blend further comprises at least one additional phthalonitrile resin. Example additional phthalonitrile resins include for instance and without limitation bis(3,4-dicyanophenyl) ether of bisphenol A, bis(2,3-dicyanophenyl) ether of bisphenol A, bis(3,4-dicyanophenyl) ether of bisphenol AP, bis(3,4-dicyanophenyl) ether of bisphenol AF, bis(3,4-dicyanophenyl) ether of bisphenol B, bis(3,4-dicyanophenyl) ether of bisphenol BP, bis(3,4- dicyanophenyl) ether of bisphenol C, bis(3,4-dicyanophenyl) ether of bisphenol C2, bis(3,4-dicyanophenyl) ether of bisphenol E, bis(3,4-dicyanophenyl) ether of bisphenol F, bis(3,4-dicyanophenyl) ether of 3,3',5,5'-tetramethylbisphenol F, bis(3,4-dicyanophenyl) ether of bisphenol FL, bis(3,4-dicyanophenyl) ether of bisphenol G, bis(3,4-dicyanophenyl) ether of bisphenol S, bis(3,4-dicyanophenyl) ether of bisphenol P, bis(3,4-dicyanophenyl) ether of bisphenol PH, bis(3,4-dicyanophenyl) ether of bisphenol TMC, bis(3,4-dicyanophenyl) ether of bisphenol Z, bis(3,4-dicyanophenyl) ether of 4,4'-dihydroxybiphenyl, bis(3,4-dicyanophenyl) ether of 4,4'-dihydroxydiphenyl ether, bis(3,4-dicyanophenyl) ether of catechol, bis(3,4-dicyanophenyl) ether of 4,4'-dihydroxybenzophenone, 3,4-dicyanophenyl ether of phenol, 2,3-dicyanophenyl ether of phenol, 4-tert-butylphthalonitrile, 4-butoxyphthalonitrile, 3,4-dicyanophenyl ether of 4-cumylphenol, 3,4-dicyanophenyl ether of 2-allylphenol, 3,4-dicyanophenyl ether of eugenol. Typically the resin blend (of two or more resins) is a solid at 25° C.

Resin blends of the disclosure optionally include one or more curatives. Such curatives often include an amine compound. Combinations of various curatives can be used if desired. The curative is typically present in an amount of between 0 and 40 percent by weight of the resin blend. Example dianiline based curatives that will promote phthalonitrile polymerization include for instance and without limitation, 4,4'-(1,3-phenylenedioxy)dianiline, 4,4'-(1,4-phenylenedioxy)dianiline, bis[4-(4-aminophenoxy)phenyl] sulfone, 4,4'-(4,4'-Isopropylidenediphenyl-1,1'-diyldioxy) dianiline, 4,4'-(1,3-Phenylenediisopropylidene)dianiline, 4,4'-(1,4-Phenylenediisopropylidene)dianiline, 4,4'-(1,1'-Biphenyl-4,4'-diyldioxy)dianiline, 4,4'-Methylenedianiline, 4,4'-Methylene-bis(2-methylaniline), 3,3'-Methylenedianiline, 3,4'-Methylenedianiline, 4,4'-Oxydianiline, 4,4'-(Isopropylidene)dianiline, 4,4'-(Hexafluoroisopropylidene)dianiline, 4,4'-(Hexafluoroisopropylidene)bis(p-phenyleneoxy)dianiline, 4,4'-Diaminobenzophenone.

Certain other optional additives may also be included, including, for example, tougheners, fillers, and combinations thereof. Such additives provide various functions. For instance, a toughening agent such as organic particles, may add strength to the composition after curing without interfering with curing. It will be understood by one of skill in the art that one compound may form two or more different functions. For example, a compound may function as both a toughening agent and a filler. In some embodiments, such additives will not react with the resins of the resin blend. In some embodiments, such additives may include reactive functional groups, particularly as end groups. Examples of such reactive functional groups include, but are not limited to, amines, thiols, alcohols, epoxides, vinyls, and combinations thereof.

Toughening agents are useful in resin blends of the present disclosure are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski). Exemplary rubbery backbones include polymerized butadiene or a polymerized mixture of butadiene and styrene. Exemplary shells including polymerized methacrylic acid esters are lower alkyl (C1-C4) substituted methacrylates. Exemplary monovinyl aromatic hydrocarbons are styrene, alpha-methylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would poison the catalyst.

Examples of useful toughening agents of the second type are acrylate core-shell graft copolymers wherein the core or backbone is a polyacrylate polymer having a glass transition temperature below 0° C., such as polybutyl acrylate or polyisooctyl acrylate to which is grafted a polymethacrylate polymer (shell) having a glass transition above 25° C., such as polymethylmethacrylate.

The third class of toughening agents useful in the invention includes elastomeric particles that have a glass transition temperature ($T_g$) below 25° C. before mixing with the other components of the composition. These elastomeric particles are polymerized from free radical polymerizable monomers and a copolymerizable polymeric stabilizer. The free radical polymerizable monomers are ethylenically unsaturated monomers or diisocyanates combined with co-reactive difunctional hydrogen compounds such as diols, diamines, and alkanolamines.

Useful toughening agents include core/shell polymers, such as methacrylate-butadiene-styrene (MBS) copolymer wherein the core is crosslinked styrene/butadiene rubber and the shell is polymethylacrylate (for example, those available under the trade names ACRYLOID KM653 and KM680, from Rohm and Haas, Philadelphia, Pa.), those having a core including polybutadiene and a shell including poly(methyl methacrylate) (for example, those available under the trade names KANE ACE M511, M521, B11A, B22, B31, and M901 from Kaneka Corporation, Houston, Tex. and CLEARSTRENGTH C223 from ATOFINA, Philadelphia, Pa.), those having a polysiloxane core and a polyacrylate shell (for example, those available under the trade names CLEARSTRENGTH S-2001 from ATOFINA and GENIOPERL P22 from Wacker-Chemie GmbH, Wacker Silicones, Munich, Germany), those having a polyacrylate core and a poly(methyl methacrylate) shell (for example, those available under the trade names PARALOID EXL2330 from Rohm and Haas and STAPHYLOID AC3355 and AC3395 from Takeda Chemical Company, Osaka, Japan), those having an MBS core and a poly(methyl methacrylate) shell (for example, those available under the trade names PARALOID EXL2691A, EXL2691, and EXL2655 from Rohm and Haas); and the like; and mixtures thereof.

As used above, for acrylic core/shell materials "core" will be understood to be an acrylic polymer having a $T_g$ of less than 0° C. and "shell" will be understood to be an acrylic polymer having a $T_g$ of greater than 25° C.

Other useful toughening agents include: carboxylated and amine terminated acrylonitrile/butadiene vulcanizable elastomer precursors, such as those available under the trade names HYCAR CTBN 1300X8, ATBN 1300X16, and HYCAR 1072 from B. F. Goodrich Chemical Co.; butadiene polymers, such as those available under the trade name HYCAR CTB; amine functional polyethers such as HCl 101 (i.e., polytetramethylene oxide diamine) a 10,000 MW, primary amine-terminated, compound from 3M Co., St. Paul, Minn., and those available under the trade name JEFFAMINE from Huntsman Chemical Co., Houston, Tex. Useful liquid polybutadiene hydroxyl terminated resins include those available under the trade names LIQUIFLEX H by Petroflex of Wilmington, Del., and HT 45 by Sartomer of Exton, PN.

Tougheners may include epoxy-terminated compounds, which can be incorporated into the polymer backbone. A typical, preferred, list of tougheners includes: acrylic core/shell polymers; styrene-butadiene/methacrylate core/shell polymers; polyether polymers; carboxylated acrylonitrile/butadienes; and carboxylated butadienes. Advantages can be obtained from the provision of the chain extension agent in a composition with an epoxy resin even in the absence of a toughening agent as described above. However, particular advantage is achieved from the presence of the toughening agent or combinations of different agents, as previously suggested.

Various combinations of toughening agents can be used if desired. If used, a toughening agent is present in the resin blend in an amount of at least 3 percent by weight, or at least 5 percent by weight. If used, a toughening agent is present in a resin blend in an amount of no greater than 35 percent by weight, or no greater than 25 weight percent.

Other optional additives, or adjuvants, may be added to the compositions as desired. Examples of such other optional additives include as colorants, anti-oxidant stabilizers, thermal degradation stabilizers, light stabilizers, flow agents, bodying agents, flattering agents, inert fillers, binders, blowing agents, fungicides, bactericides, surfactants, plasticizers, rubber tougheners, and other additives known to those skilled in the art. Such additives are typically substantially unreactive. These adjuvants, if present, or other optional additives, are added in an amount effective for their intended purpose.

Examples of suitable filler materials include reinforcement-grade carbon black, fluoroplastics, clays, and any combination of any of these in any proportions.

The phrase "reinforcement-grade carbon black" as used herein, includes any carbon black with an average particle size smaller than about 10 microns. Some particularly suitable average particle sizes for reinforcement-grade carbon black range from about 9 nm to about 40 nm. Carbon black that is not reinforcement grade include carbon black with an average particle size larger than about 40 nm. Carbon nanotubes are also useful fillers. Carbon black fillers are typically employed as a means to balance, elongation, hardness, abrasion resistance, conductivity, and processibility of compositions. Suitable examples include MT blacks (medium thermal black) designated N-991, N-990, N-908, and N-907; FEF N-550; and large particle size furnace blacks.

Other useful fillers include diatomaceous earth, barium sulfate, talc, and calcium fluoride. The choice and amounts of optional components depend on the needs of the specific application.

Reaction conditions for curing the composition depend on the reactants and amounts used and can be determined by those skilled in the art. The curable compositions are made by mixing in any order resorcinol diphthalonitrile ether resin and bisphenol M diphthalonitrile ether resin and/or a bisphenol T diphthalonitrile ether resin, as described above. Generally, the composition is then heated to a temperature between about 50° C. and 350° C., preferably between about 130-350° C., for a time of about 1-480 minutes. Some blends containing a greater portion of phthalonitrile resin may require a post cure at temperatures up to 350° C. to achieve ultimate performance.

Suitable sources of heat to cure the compositions of the invention include induction heating coils, ovens, hot plates, heat guns, infrared sources including lasers, microwave sources.

Solvents can be used as a processing aid. Useful solvents are ketones such as acetone, methyl ethyl ketone, methyl isobutyl ketone, cyclopentanone and cyclohexanone; amides such as acetamide, formamide, N,N-dimethylforamide, N-methylpyrrolidinone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl)ethanol, 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, methyl cellosolve acetate, methyl formate; and other solvents such as tetrahydrofuran, methylene chloride, dichloromethane, chloroform, acetonitrile, nitromethane, glycol sulfite and 1,2-dimethoxyethane (glyme).

Various embodiments are provided that include resin blends.

Embodiment 1 is a resin blend comprising a blend of resorcinol diphthalonitrile ether resin and a bisphenol M diphthalonitrile ether resin. The bisphenol M diphthalonitrile ether resin is of Formula I:

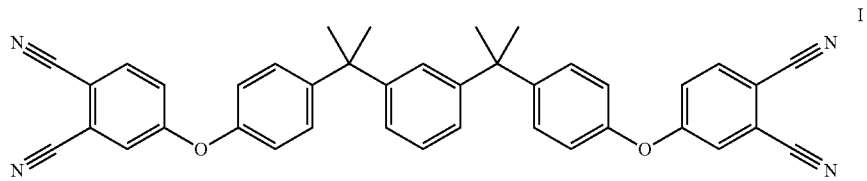 [SMILES: CC(C)(c1ccc(Oc2ccc(C#N)c(C#N)c2)cc1)c1cccc(C(C)(C)c2ccc(Oc3ccc(C#N)c(C#N)c3)cc2)c1]

Embodiment 2 is the resin blend of embodiment 1, wherein a weight ratio of the resorcinol diphthalonitrile ether resin to the bisphenol M diphthalonitrile ether resin ranges from 10:90 to 90:10, inclusive.

Embodiment 3 is the resin blend of embodiment 1 or embodiment 2, wherein a weight ratio of the resorcinol diphthalonitrile ether resin to the bisphenol M diphthalonitrile ether resin ranges from 15:85 to 85:15, inclusive.

Embodiment 4 is the resin blend of any of embodiments 1 to 3, wherein a weight ratio of the resorcinol diphthalonitrile ether resin to the bisphenol M diphthalonitrile ether resin ranges from 30:70 to 70:30, inclusive.

Embodiment 5 is the resin blend of any of embodiments 1 to 4, further comprising at least one additive.

Embodiment 6 is the resin blend of embodiment 5, wherein the at least one additive is selected from a catalyst, a curative, a toughener, a filler, and combinations thereof.

Embodiment 7 is the resin blend of embodiment 6, wherein the curative comprises an amine.

Embodiment 8 is the resin blend of embodiment 5 or embodiment 6, wherein the curative comprises an aniline functional residue.

Embodiment 9 is the resin blend of any of embodiment 6 to 8, wherein the curative comprises 4,4'-(1,3-phenylenedioxy)dianiline.

Embodiment 10 is the resin blend of any of embodiments 6 to 9, wherein the curative is present in an amount of between 0 and 40 percent by weight of the resin blend.

Embodiment 11 is the resin blend of any of embodiments 6 to 10, wherein the at least one additive comprises a toughener.

Embodiment 12 is the resin blend of any of embodiments 1 to 11, wherein the resin blend is a solid at 25° C.

Embodiment 13 is the resin blend of any of embodiments 1 to 12, wherein the resin blend further comprises at least one additional phthalonitrile resin.

Embodiment 14 is a resin blend comprising a blend of resorcinol diphthalonitrile ether resin and a bisphenol T diphthalonitrile ether resin, wherein the bisphenol T diphthalonitrile ether resin is of Formula II:

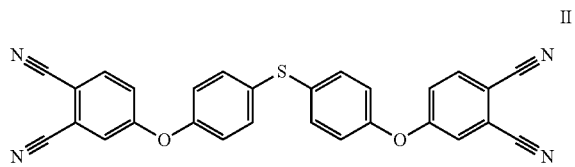 [SMILES: N#Cc1ccc(Oc2ccc(Sc3ccc(Oc4ccc(C#N)c(C#N)c4)cc3)cc2)cc1C#N]

Embodiment 15 is the resin blend of embodiment 14, wherein a weight ratio of the resorcinol diphthalonitrile ether resin to the bisphenol T diphthalonitrile ether resin ranges from 10:90 to 90:10, inclusive.

Embodiment 16 is the resin blend of embodiment 14 or embodiment 15, wherein a weight ratio of the resorcinol diphthalonitrile ether resin to the bisphenol T diphthalonitrile ether resin ranges from 15:85 to 15:85, inclusive.

Embodiment 17 is the resin blend of any of embodiments 14 to 16, wherein a weight ratio of the resorcinol diphthalonitrile ether resin to the bisphenol T diphthalonitrile ether resin ranges from 30:70 to 70:30, inclusive.

Embodiment 18 is the resin blend of any of embodiments 14 to 17, further comprising at least one additive.

Embodiment 19 is the resin blend of embodiment 18, wherein the at least one additive is selected from a catalyst, a curative, a toughener, a filler, and combinations thereof.

Embodiment 20 is the resin blend of embodiment 19, wherein the curative comprises an amine.

Embodiment 21 is the resin blend of embodiment 19 or embodiment 20, wherein the curative comprises an aniline functional residue.

Embodiment 22 is the resin blend of any of embodiments 19 to 21, wherein the curative comprises 4,4'-(1,3-phenylenedioxy)dianiline.

Embodiment 23 is the resin blend of any of embodiments 19 to 22, wherein the curative is present in an amount of between 0 and 40 percent by weight of the resin blend.

Embodiment 24 is the resin blend of any of embodiments 19 to 23, wherein the at least one additive comprises a toughener.

Embodiment 25 is the resin blend of any of embodiments 14 to 24, wherein the resin blend is a solid at 25° C.

Embodiment 26 is the resin blend of any of embodiments 14 to 25, wherein the resin blend further comprises at least one additional phthalonitrile resin.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims. Unless otherwise noted, all chemicals used in the examples can be obtained from Sigma-Aldrich Corp. (Saint Louis, Mo.)

Methods:

Method of Measuring Cure Reaction Exotherm Via Differential Scanning Calorimeter (DSC)

A TA Instruments Q Series DSC (obtained from TA Instruments, New Castle, Del.) was used. Approximately 5 mg of resin was weighed into an aluminum DSC pan. The sample pan was loaded into the DSC instrument, and the heat flow of the sample was measured in a dynamic DSC measurement with a thermal ramp rate of either 1 degrees Celsius per minute (° C./min) or 10° C./min.

Method of Measuring Stiffness (E') and Glass Transition Temperature (tan δ Peak) Via Dynamic Mechanical Analyzer (DMA)

A TA Instruments Q Series DMA (obtained from TA Instruments, New Castle, Del.) was used. Dynamic mechanical measurements were performed using ether single cantilever beam geometry or tensile geometry. The low strain in-phase and out-of-phase deformation response was measured when applying an oscillatory controlled force with a controlled deformation amplitude of 20 um at a frequency of 1 Hz, and the resulting storage and loss moduli and loss tangent were calculated. The temperature was ramped at either 3° C./min or 5° C./min over a temperature range spanning the glass to rubber transition.

Method of Measuring Weight Loss Via Thermogravimetric Analysis (TGA)

A TA Instruments Q Series TGA (obtained from TA Instruments, New Castle, Del.) was used. Samples of approximately 5-10 mg were loaded on platinum pans into the TGA. The mass loss of the sample was measured under an air atmosphere and under a nitrogen atmosphere with a thermal ramp of 1° C./min.

Preparatory Example A (BMPN)

Bisphenol M diphthalonitrile ether (i.e., bis(3,4-dicyanophenyl) ether of bisphenol M) was derived from the nucleophilic substitution reaction of 4-nitrophthalonitrile and bisphenol M. To a three necked 500 mL reaction flask was added 18 g (0.104 mol) of 4-nitrophthalonitrile, 18.02 g (0.52 mol) of bisphenol M, 28.74 g (0.208 mol) of anhydrous $K_2CO_3$, and 180 g of dry DMSO) and stirred for 48 hours at room temperature under a nitrogen atmosphere. The reaction solution was poured into 600 mL of stirring deionized water, leaving undissolved salts behind in the reaction flask. The precipitated product was collected on a Buchner funnel by suction filtration. The precipitate was added to 200 mL of methanol and stirred for 30 minutes to remove impurities. The solid product was collected a second time on a Buchner funnel by suction filtration and washed with 200 ml of methanol. The product was collected and dried in a convection oven at 120° C. The product, 28.42 g (91.3%), had a melt temperature of 160° C. and was identified as the desired compound by infrared analysis.

Preparatory Example B (RPN)

Resorcinol diphthalonitrile ether (i.e., bis(3,4-dicyanophenyl) ether of resorcinol) was derived from the nucleophilic substitution reaction of 4-nitrophthalonitrile and resorcinol. To a three necked 500 mL reaction flask was added 18 g (0.104 mol) of 4-nitrophthalonitrile, 5.72 g (0.52 mol) of resorcinol, 28.74 g (0.208 mol) of anhydrous $K_2CO_3$, and 180 g of dry DMSO) and stirred for 48 hours at room temperature under a nitrogen atmosphere. The reaction solution was poured into 600 mL of stirring deionized water, leaving undissolved salts behind in the reaction flask. The precipitated product was collected on a Buchner funnel by suction filtration. The precipitate was added to 200 mL of methanol and stirred for 30 minutes to remove impurities. The solid product is collected a second time on a Buchner funnel by suction filtration and washed with 200 ml of methanol. The product was collected and dried in a convection oven at 120° C. The product, 17 g (90.3%), had a melt temperature of 185° C. and was identified as the desired compound by infrared analysis.

Preparatory Example C (BTPN)

Bisphenol T diphthalonitrile ether (i.e., bis(3,4-dicyanophenyl) ether of bisphenol T) was derived from the nucleophilic substitution reaction of 4-nitrophthalonitrile and bisphenol T. To a three necked 500 mL reaction flask was added 18 g (0.104 mol) of 4-nitrophthalonitrile, 11.34 g (0.52 mol) of bisphenol T, 28.74 g (0.208 mol) of anhydrous $K_2CO_3$, and 180 g of dry DMSO) and stirred for 48 hours at room temperature under a nitrogen atmosphere. The reaction solution was poured into 600 mL of stirring deionized water, leaving undissolved salts behind in the reaction flask. The precipitated product was collected on a Buchner funnel by suction filtration. The precipitate was added to 200 mL of methanol and stirred for 30 minutes to remove impurities. The solid product was collected a second time on a Buchner funnel by suction filtration and washed with 200 ml of methanol. The product was collected and dried in a convection oven at 120° C. The product, 21.6 g (89.1%), had a melt temperature of 178° C. and was identified as the desired compound by infrared analysis.

Preparatory Example D (BPPN)

Bisphenol P diphthalonitrile ether (i.e., bis(3,4-dicyanophenyl) ether of bisphenol P) was derived from the nucleophilic substitution reaction of 4-nitrophthalonitrile and bisphenol M. To a three necked 250 mL reaction flask was added 9.1 g (0.052 mol) of 4-nitrophthalonitrile, 9.11 g (0.026 mol) of bisphenol M, 14.53 g (0.105 mol) of anhydrous $K_2CO_3$, and 90 g of dry DMSO) and stirred for 48 hours at room temperature under a nitrogen atmosphere. The reaction solution was poured into 300 mL of stirring deionized water, leaving undissolved salts behind in the reaction flask. The precipitated product was collected on a Buchner funnel by suction filtration. The precipitate was added to 100 mL of methanol and stirred for 30 minutes to remove impurities. The solid product was collected a second time on a Buchner funnel by suction filtration and washed with 100 ml of methanol. The product was collected and dried in a convection oven at 120° C. The product, 13.2 g (83.9%), had a melt temperature of 213° C. and was identified as the desired compound by infrared analysis.

Example 1 (Ex 1)

BMPN/RPN(2/1) Blend 8.0 g of BMPN and RPN in a 2/1 mass ratio were melt blended at a temperature of 190° C. in a flat bottom 70 mm diameter thin gauge aluminum pan. 4,4'-(1,3-phenyleneoxy) aniline was added to the resin blend at 4 parts per hundred resin (pph) by mass and stirred into the resin at 190° C. The resin was placed in an air circulating oven and cured for 2 hours at 230° C. and 5 hours at 300° C., ramping 3 degrees Celsius per minute (° C./min) between set points. The resin underwent a thermosetting network polymerization to a hard stiff solid. The solid was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 350° C. under an inert nitrogen atmosphere, and subjected to a second DMA measurement up to 350° C., monitoring for a change in the specimen mechanical response due to residual cure. No change was witnessed in the mechanical response. The data for Example 1 is provided in Table 1A below.

Example 2 (Ex 2)

BTPN/RPN(2/1) Blend 8.0 g of BTPN and RPN in a 2/1 mass ratio were melt blended at a temperature of 190° C. in a flat bottom 70 mm diameter thin gauge aluminum pan. 4,4'-(1,3-phenyleneoxy) aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was further post cured at 350° C. for 1 hour under a flow of nitrogen in a tube furnace, ramping 3° C./min between set points, then cooled at 5° C./min to 40° C. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 375° C. under an inert nitrogen atmosphere, and subjected to a second DMA measurement up to 350° C., monitoring for a change in the specimen mechanical response due to residual cure. No change was witnessed in the mechanical response. The data for Example 2 is provided in Table 1C below.

Example 3 (Ex 3)

BTPN/RPN(1/2) Blend 8.0 g of BTPN and RPN in a 1/2 mass ratio were melt blended at a temperature of 190° C. in a flat bottom 70 mm diameter thin gauge aluminum pan. 4,4'-(1,3-phenyleneoxy) aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was further post cured at 350° C. for 1 hour and 375° C. for 1 hour under a flow of nitrogen in a tube furnace ramping 3° C./min between set points, then cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 400° C. at 3° C./min, monitoring for a change in the specimen mechanical response due to residual cure. No change was witnessed in the mechanical response. The data for Example 3 is provided in Table 1C below.

Example 4 (Ex 4)

BMPN/RPN(1/1) Blend 8.0 g of BMPN and RPN in a 1/1 mass ratio were melt blended at a temperature of 190° C. in a flat bottom 70 mm diameter thin gauge aluminum pan. 4,4'-(1,3-phenyleneoxy) aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was further post cured at 350° C. for 1 hour and 375° C. for 1 hour under a flow of nitrogen in a tube furnace ramping 3° C./min between set points, then cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 400° C. at 3° C./min, monitoring for a change in the specimen mechanical response due to residual cure. No change was witnessed in the mechanical response. The data for Example 4 is provided in Table 1A below.

Example 5 (Ex 5)

BMPN/RPN(1/2) Blend 8.0 g of BMPN and RPN in a 1/2 mass ratio were melt blended at a temperature of 190° C. in a flat bottom 70 mm diameter thin gauge aluminum pan. 4,4'-(1,3-phenyleneoxy) aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was further post cured at 350° C. for 1 hour and 375° C. for 1 hour under a flow of nitrogen in a tube furnace ramping 3° C./min between set points, then cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 400° C. at 3° C./min, monitoring for a change in the specimen mechanical response due to residual cure. No change was witnessed in the mechanical response. The data for Example 5 is provided in Table 1A below.

Example 6 (Ex 6)

BMPN/BTPN(2/1) Blend 8.0 g of BMPN and BTPN in a 2/1 mass ratio were melt blended at a temperature of 190° C. in a flat bottom 70 mm diameter thin gauge aluminum pan. 4,4'-(1,3-phenyleneoxy) aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 350° C. under an inert nitrogen atmosphere, and subjected to a second DMA measurement up to 350° C., monitoring for a change in the specimen mechanical response due to residual cure. No change was witnessed in the mechanical response. The data for Example 8 is provided in Table 1D below.

Example 7 (Ex 7)

BMPN/BPPN(2/1) Blend 8.0 g of BMPN and BPPN in a 2/1 mass ratio were melt blended at a temperature of 230° C. in a flat bottom 70 mm diameter thin gauge aluminum pan. 4,4'-(1,3-phenyleneoxy) aniline was added to the resin blend at 4 pph by mass and stirred into the resin at 230° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 350° C. under an inert nitrogen atmosphere, and subjected to a second DMA measurement up to 350° C., monitoring for a change in the specimen mechanical response due to residual cure. No change was witnessed in the mechanical response. The data for Example 8 is provided in Table 1D below.

Example 8 (Ex 8)

BMPN/BTPN/RPN(1/1/1) Blend 8.0 g of BMPN, BTPN and RPN in a 1/1/1 mass ratio were melt blended at a temperature of 190° C. in a flat bottom 70 mm diameter thin gauge aluminum pan. 4,4'-(1, 3-phenyleneoxy)aniline was added to the resin blend at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was further post cured at 350° C. for 1 hour and 375° C. for 1 hour under a flow of nitrogen in a tube furnace, ramping 3° C./min between set points and cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 400° C. at 3° C./min, monitoring for a change in the specimen mechanical response due to residual cure. No change was witnessed in the mechanical response. The data for Example 8 is provided in Table 1D below.

Comparative Example 1 (CE 1)

RPN 8.0 g of RPN was melted at a temperature of 190° C. in a flat bottom 70 mm diameter thin gauge aluminum pan. 4,4'-(1,3-phenyleneoxy)aniline was added to the resin at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid sample was cooled at 5° C./min to 40° C. and removed from the aluminum pan. The sample was further post cured at 350° C. for 1 hour, 375° C. for 1 hour, and 400° C. for 30 minutes under a flow of nitrogen in a tube furnace, ramping 3° C./min between set points and cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 450° C. at 3° C./min, monitoring for residual cure at higher temperatures. The specimen showed evidence of increased stiffness at temperatures over 400° C. on the second heating ramp. The data for Comparative Example 1 is provided in each of Tables 1A, 1B, and 1C below.

Comparative Example 2 (CE 2)

BTPN 8.0 g of BTPN was melted at a temperature of 190° C. in a flat bottom 70 mm diameter thin gauge aluminum pan. 4,4'-(1,3-phenyleneoxy)aniline was added to the resin at 4 pph by mass and stirred into the resin at 190° C. The resin was placed in an air circulating oven and cured for 2 hours at 230° C. and 5 hours at 300° C., ramping 3° C./min between set points. The resin underwent a thermosetting network polymerization to a hard stiff solid. The solid sample was cooled at 5° C./min to 40° C. and removed from the aluminum pan. The sample was further post cured at 350° C. for 1 hour under a flow of nitrogen in a tube furnace and cooled at 5° C./min to 40° C. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 375° C. under an inert nitrogen atmosphere, and subjected to a second DMA measurement up to 350° C., monitoring for a change in the specimen mechanical response due to residual cure. No change was witnessed in the mechanical response. The data for Comparative Example 2 is provided in Table 1C below.

Comparative Example 3 (CE 3)

BPPN 8.0 g of BPPN was melted at a temperature of 230° C. in a flat bottom 70 mm diameter thin gauge aluminum pan. 4,4'-(1,3-phenyleneoxy)aniline was added to the resin blend at 4 pph by mass and stirred into the resin at 230° C. The resin was placed in an air circulating oven and cured for 2 hours at 230° C. and 5 hours at 300° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 1 hour at 375° C. under an inert nitrogen atmosphere, and subjected to a second DMA measurement up to 350° C., monitoring for a change in the specimen mechanical response due to residual cure. No change was witnessed in the mechanical response. The data for Comparative Example 3 is provided in Table 1B below.

Comparative Example 4 (CE 4)

BMPN 8.0 g of BMPN was melted at a temperature of 190° C. in a flat bottom 70 mm diameter thin gauge aluminum pan. 4,4'-(1,3-phenyleneoxy)aniline was added to the resin at 4 pph by mass and stirred into the resin at 190° C. The resin was placed in an air circulating oven and cured for 15 hours at 230° C. and 5 hours at 300° C., ramping 3° C./min between set points. The resin underwent a thermosetting network polymerization to a hard stiff solid. The solid sample was cooled at 5° C./min to 40° C. and removed from the aluminum pan. The sample was cut into strips for DMA measurement of the stiffness (E') and glass transition temperature (tan δ peak) in single cantilever beam geometry. A DMA specimen was subjected to a thermal heating ramp up to 350° C. at 3° C./min. The specimen was further post cured for 2 hours at 350° C. under an inert nitrogen atmosphere, and subjected to a second DMA measurement up to 350° C., monitoring for a change in the specimen mechanical response due to residual cure. No change was witnessed in the mechanical response. The data for Comparative Example 4 is provided in Table 1A below.

Comparative Example 5 (CE 5)

BPPN/RPN(2/1) Blend 8.0 g of BPPN and RPN in a 2/1 mass ratio were melt blended at a temperature of 230° C. in a flat bottom 70 mm diameter thin gauge aluminum pan. 4,4'-(1,3-phenyleneoxy)aniline was added to the resin blend at 4 pph by mass and stirred into the resin at 230° C. The resin was placed in an air circulating oven and cured for 2 hours at 230° C. and 5 hours at 300° C., ramping 3° C./min between set points. The resin underwent a thermosetting network polymerization to a hard stiff solid. The solid was cooled at 5° C./min to 40° C. and removed from the aluminum pan. The sample was further post cured at 375° C. for 2 hours under a flow of nitrogen in a tube furnace, ramping 3° C./min between set points and cooled at 5° C./min to 40° C. The sample was cut into strips for DMA measurement of the stiffness (E') and glass transition temperature (tan δ peak) in single cantilever beam geometry. A DMA specimen was subjected to two thermal heating ramps up to 400° C. at 3° C./min, monitoring for a change in the specimen mechanical response due to residual cure. No change was witnessed in the mechanical response. The data for Comparative Example 5 is provided in Table 1B below.

TABLE 1A

Blends of BMPN and RPN

| | Resin Blend | | DMA (cantilever, 3° C./min ram | | | |
|---|---|---|---|---|---|---|
| | | | E' (25° C.) | Tg (E' onset) | Tg (E" peak) | Tg (tan δ peak) |
| Example | Composition | mass % | [MPa] | [° C.] | [° C.] | [° C.] |
| CE 4 | BMPN | 0 (R) | 2840 | 209 | 213 | 229 |
| Ex 1 | BMPN/RPN (2/1) | 33.3 (R) | 2844 | 240 | 245 | 271 |
| Ex 4 | BMPN/RPN (1/1) | 50.0 (R) | 3360 | 281 | 300 | 320 |
| Ex 5 | BMPN/RPN (1/2) | 66.7 (R) | 2950 | 330 | 344 | 381 |
| CE 1 | RPN | 100 (R) | 3560 | 412 | >450 | >450 |

TABLE 1B

Blends of BPPN with RPN

| | Resin Blend | | DMA (cantilever, 3° C./min ram | | | |
|---|---|---|---|---|---|---|
| | | | E' (25° C.) | Tg (E' onset) | Tg (E" peak) | Tg (tan δ peak) |
| Example | Composition | mass % | [MPa] | [° C.] | [° C.] | [° C.] |
| CE 3 | BPPN | 0 (R) | 2560 | 264 | 268 | 287 |
| CE 5 | BPPN/RPN (2/1) | 33.3 (R) | 2800 | 365 | 375 | 422 |
| CE 1 | RPN | 100 (R) | 3560 | 412 | >450 | >450 |

TABLE 1C

Blends of BTPN with RPN

| | Resin Blend | | DMA (cantilever, 3° C./min ramp) | | | |
|---|---|---|---|---|---|---|
| | | | E' (25° C.) | Tg (E' onset) | Tg (E" peak) | Tg (tan δ peak) |
| Example | Composition | mass % | [MPa] | [° C.] | [° C.] | [° C.] |
| CE 2 | BTPN | 0 (R) | 2630 | 279 | 289 | 312 |
| Ex 2 | BTPN/RPN (2/1) | 33.3 (R) | 2610 | 289 | 297 | 330 |
| Ex 3 | BTPN/RPN (1/2) | 66.7 (R) | 3110 | 323 | 331 | 364 |
| CE 1 | RPN | 100 (R) | 3560 | 412 | >450 | >450 |

TABLE 1D

Blend of BMPN, BTPN, RDPN

| | Resin Blend | | DMA (cantilever, 3° C./min ramp) | | | |
|---|---|---|---|---|---|---|
| | | | E' (25° C.) | Tg (E' onset) | Tg (E" peak) | Tg (tan δ peak) |
| Example | Composition | mass % | [MPa] | [° C.] | [° C.] | [° C.] |
| Ex 6 | BMPN/BTPN (2/1) | 66.7 (BM) | 2745 | 235 | 238 | 259 |
| Ex 7 | BMPN/BPPN (2/1) | 66.7 (BM) | 2724 | 230 | 232 | 253 |
| Ex 8 | BMPN/BTPN/RPN (1/1/1) | 33.3 (BM) | 2520 | 335 | 354 | 381 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A resin blend comprising a blend of resorcinol diphthalonitrile ether resin and a bisphenol M diphthalonitrile ether resin, wherein the bisphenol M diphthalonitrile ether resin is of Formula I:

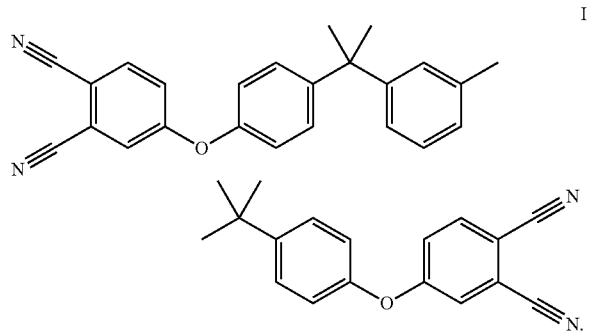

2. The resin blend of claim 1, wherein a weight ratio of the resorcinol diphthalonitrile ether resin to the bisphenol M diphthalonitrile ether resin ranges from 10:90 to 90:10, inclusive.

3. The resin blend of claim 1, further comprising at least one additive selected from a catalyst, a curative, a toughener, a filler, and combinations thereof.

4. The resin blend of claim 3, wherein the curative comprises an amine.

5. The resin blend of claim 3, wherein the curative comprises an aniline functional residue.

6. The resin blend of claim 5, wherein the curative comprises 4,4'-(1,3-phenylenedioxy)dianiline.

7. The resin blend of claim 1, wherein the resin blend further comprises at least one additional phthalonitrile resin.

8. A resin blend comprising a blend of resorcinol diphthalonitrile ether resin and a bisphenol T diphthalonitrile ether resin, wherein the bisphenol T diphthalonitrile ether resin is of Formula II:

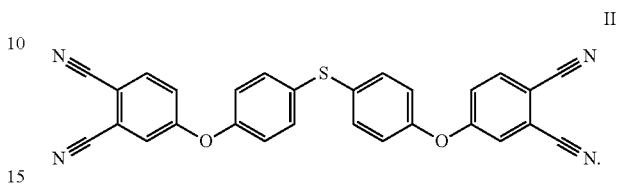

9. The resin blend of claim 8, wherein a weight ratio of the resorcinol diphthalonitrile ether resin to the bisphenol T diphthalonitrile ether resin ranges from 10:90 to 90:10, inclusive.

10. The resin blend of claim 8, further comprising at least one additive selected from a catalyst, a curative, a toughener, a filler, and combinations thereof.

11. The resin blend of claim 10, wherein the curative comprises an amine.

12. The resin blend of claim 10, wherein the curative comprises an aniline functional residue.

13. The resin blend of claim 10, wherein the curative comprises 4,4'-(1,3-phenylenedioxy)dianiline.

14. The resin blend of claim 8, wherein the resin blend further comprises at least one additional phthalonitrile resin.

* * * * *